United States Patent [19]
Duncan et al.

[11] Patent Number: 5,679,223
[45] Date of Patent: Oct. 21, 1997

[54] METHOD FOR SEPARATING AND PURIFYING CATECHOL MIXTURES

[75] Inventors: David H. Duncan, Beulah; Gene G. Baker, Hazen; Dana J. Maas, Hazen; Kevin M. Mohl, Hazen; Alfred K. Kuhn, Beulah, all of N. Dak.

[73] Assignee: Dakota Gasification Company, Beulah, N. Dak.

[21] Appl. No.: 490,780

[22] Filed: Jun. 15, 1995

[51] Int. Cl.⁶ .................. B01D 3/40; C07C 37/80
[52] U.S. Cl. .................. 203/64; 203/74; 203/75; 203/77; 203/78; 203/80; 568/750; 568/753; 568/869
[58] Field of Search .................. 203/64, 74, 75, 203/78, 77, 80, 63; 568/749, 869, 753, 750, 766, 751

[56] References Cited

U.S. PATENT DOCUMENTS

| | | | |
|---|---|---|---|
| 2,789,145 | 4/1957 | Neuworth | 568/759 |
| 3,169,101 | 2/1965 | Berthoux et al. | 203/59 |
| 3,331,755 | 7/1967 | Neuworth | 203/59 |
| 4,424,381 | 1/1984 | Leston | 568/753 |
| 4,503,267 | 3/1985 | Pavlin | 568/753 |
| 5,354,429 | 10/1994 | Duncan et al. | 203/59 |

FOREIGN PATENT DOCUMENTS

| | | |
|---|---|---|
| 209 185 | 4/1984 | Germany. |
| 0678191 | 8/1952 | United Kingdom. |
| 730473 | 5/1955 | United Kingdom. |

OTHER PUBLICATIONS

Chemical Abstract Citation 90: 60311r, "Selective Extraction of Pyrocatechol and Its Homologs from Coal Pyrolysis Products" (1978).

Chemical Abstract Citation 90: 54658x, "Separation of Pyrocatechol" (1979).

Chemical Abstract Citation 50: 6776i, "Separation of 3-Methylpyrocatechol from Pyrocatechol" (1956).

(List continued on next page.)

*Primary Examiner*—Virginia Manoharan
*Attorney, Agent, or Firm*—Chilton, Alix & Van Kirk

[57] ABSTRACT

An extractive distillation process using a high boiling polyol such as glycerol is employed for separating high purity catechol, 3-methylcatechol and 4-methylcatechol from a high boiling, pitch-like dihydric phenol fraction. Fractional distillation first separates an impure overhead mixture of the catechol and 3-methylcatechol and an impure 4-methylcatechol bottoms. The impure overhead is extractively distilled to remove impurities and then extractively distilled again to separate the catechol and 3-methylcatechol. This produces a pure overhead of 3-methylcatechol and a bottoms of catechol and polyol which is distilled to recover the catechol and recycle the polyol. The impure 4-methylcatechol is distilled to remove residual material and then extractively distilled to remove impurities. The resulting mixture of 4-methylcatechol and polyol is distilled to recover the pure 4-methylcatechol and to recycle the polyol.

16 Claims, 3 Drawing Sheets

OTHER PUBLICATIONS

Chemical Abstract Citation 70: 108130b, "Recovering Pyrocatechol and Homologs, Free Neutral Oils and Bases, from Tar Fractions" (1969).

Chemical Abstract Citation 49: 7225c, "Recovery of Catechol from Low Temperature Tar" (1955).

Chemical Abstract Citation 95: 61764k, "Purification of Pyrocatechol" (1981).

Chemical Citation Abstract 84: 89818c, "Modified Extraction Distillation of Higher-Boiling Phenol Mixtures".

Chemical Citation Abstract, 104: 186131n, "Isolation of Pyrocatechol and Homologs from Phenol Mixtures".

Chemical Citation Abstract 113: 5861r, "Continuous Separation of Pyrocatechol-Rich Fractions From Phenoslocan Extracts and/or Phenosolvan Extract Residues".

Chemical Citation Abstract 113: 5862s, "Separation of Pyrocatechol-Rich Fractions from Phenol- and Polyphenol-Containing Mixtures".

Chemical Citation Abstract 113: 58683t, "Continuous Separation of Pyrocatechol-Rich Fractions from Phenol- and Polyphenol-Containing Mixtures".

Chemical Citation Abstract 104: 226658, "Intensified Economical Processign of Phenol Solvent Extracts from Phenosolvan Wastes of Low Temperature Brown Coal Coking Plants".

METHOD FOR SEPARATING AND PURIFYING CATECHOL MIXTURES

The present invention relates to a method for the separation and purification of catechol, 3-methylcatechol and/or 4-methylcatechol, to isolate these as commercial grade products from a high boiling phenolic mixture.

BACKGROUND OF THE INVENTION

High boiling phenolic mixtures containing dihydric phenols may be obtained from a variety of sources. For example, such phenolic mixtures may be obtained as a bottoms product from the depitching (by distillation) of a material known as Phenosolvan extract, which is derived from the solvent extraction of phenolics from gas liquor streams which are produced as a by-product of coal gasification. A typical Phenosolvan extract mixture usually contains monohydric phenols (such as those found in cresylic acid), dihydric phenols (such as catechol and its homologues), neutral oil, tar bases, water and pitch-like material. Materials similar to Phenosolvan extract may also be obtained by way of other solvent extraction processes designed to extract phenolics from by-product waste water from coal devolatilization technologies of various kinds. Alternately, high boiling dihydric phenol mixtures may be obtained as by-products of pulp mill processes, wood carbonization, or various synthetic reactions such as reactions whereby phenol is hydroxylated to form mixtures of hydroquinone and catechol.

Various prior art methods for isolating and purifying catechols from mixtures of dihydric phenols consist of various combinations of distillation operations and crystallization or selective precipitation processes, as well as a number of methods which utilize the tendency of catechol to co-distill with hydrocarbons of selected boiling ranges. The following summarizes the known prior art in the field.

East German Patent No. 209,185 (1982) describes a method which utilizes fractional distillation to isolate a distillate rich in catechol. Given that it is difficult to separate catechol from 3-methylcatechol by fractionation (the latter behaves in fractionation in a manner which suggests it is slightly higher boiling than catechol), various cuts in which the 3-methylcatechol content is minimized as much as possible are recycled to the front end of the process, to ultimately obtain as good a recovery of catechol as possible. The catechol-rich distillate fraction, which is as "narrow band" as possible (e.g., low in 3-methylcatechol content), is crystallized and recrystallized from toluene, to obtain a catechol product.

Chemical Abstracts citation 90: 6031r describes a method developed in the former USSR and published in 1978, which is based on the ability of calcium to selectively precipitate catechol from water solutions of catechols. From this abstract we find that 3-methylcatechol has much less a tendency to form an insoluble calcium salt, than catechol. Although not specified in the abstract, this precipitate of calcium catecholate is then (one would assume, based on familiarity with this field) reacted with hydrochloric acid to obtain a solution of catechol and calcium chloride, from which the catechol, enhanced in purity, is obtained (such as, for example, by extraction into a solvent, and subsequent crystallization). This is similar to the method found in Chemical Abstracts citation 90: 54658x, which describes USSR Patent No. 632,682 (1977), which also makes use of the calcium salt of catechol as a means of purification.

A 1954 Czechoslovakian Patent, No. 83,691 (for dihydric phenols from coal tar, peat tar and products of wood carbonization), and a 1968 Czechoslovakian Patent, No. 128,367 (for dihydric phenols from "phrenolsolvane" [sic] tar extract), describe methods very similar to the above-described Soviet techniques, also based on calcium catecholate precipitation (see Chemical Abstracts citations 50: 6776i and 70: 108130b, respectively).

An article in "Chemistry and Industry" from 1955, by A. Fowler Williams, describes a method which utilizes an extraction of a solution of low temperature tar in benzene with sodium bicarbonate solution. From the extract, "crude acids" (dihydric phenols) are recovered, and are then fractionated to give a distillate from which catechol is crystallized (see Chemical Abstracts citation 49: 7225c).

The Koppers Company, Inc., (Leston, Gerd) patented a method (U.S. Pat. No. 4,424,381, Jan. 3, 1984) for separation of dihydric phenols by treating a mixture of dihydric phenols with calcium, lithium or magnesium salts, and an aliphatic ether, so as to obtain a complex with one of the phenols. This complex, after isolation, was decomposed to provide the target compound.

Chemical Abstract Citation 95: 61764k describes USSR Patent No. 825,485, wherein catechol was purified by extractive distillation with chlorobenzene, followed by crystallization from the solvent. Given that chlorobenzene is not a polyol and could not function as a polyol (it does not provide hydrogen bonding with the catechol), the mechanism utilized in this method is altogether different from the present invention. The mechanism obtained with chlorobenzene may be similar to that obtained with hydrocarbons (see the following three paragraphs).

Czechoslovakian Patent No. 159,097, June 15, 1975, describes an extractive distillation method for separation of catechol and its alkyl derivatives, based on (from Chemical Abstract 84: 89818c) "feeding vapors of an extracting agent countercurrent to the phenol feed. Steam, octyl alcohol, and a hydrocarbon fraction, b. [boiling at] 160°–240°, were used in the examples. Pyrocatechols comprised 80–92% of the sepd. compds. versus 50% without the extn. agent". This is very different from the present invention, since in the Czechoslovakian method, the extracting agent is fed in the vapor phase, countercurrent to the phenolic feed, whereas in the present invention, the extraction agent is virtually 100% in the liquid phase and descends in the column, rather than ascends (as must the hydrocarbon used in the Czechoslovakian method). It follows, then, that the mechanism by which this Czechoslovakian invention operates is not the same as that by which the present invention operates. As found in the following citation, other Czechoslovakians, in 1986, developed what could be termed a further refinement of the above method, very similar to it.

Chemical Abstract Citation 104: 186131n describes Czechoslovakian Patent CS 221,373 in the following words: "From the phenolic fractions of C[oal] gasification and carbonization processes, the title compounds (pyrocatechol and homologues) were distd. together with an auxiliary hydrocarbon fraction b. 180°–250°. Thus, 100 kg phenol conc. was distd. with 700 kg of a petroleum distn. fraction b. 170°–190° in a 10-plate column at reflux ratio 1:5 and head temp. <190°. From the cooled distillate, 29 kg pyrocatechol of 99% purity crystd. in 80.87% yield". In this invention, the catechol codistills with the hydrocarbon. This is a distinctly different operation than the present invention.

Chemical Abstracts Citations 113: 5861r, 113: 5862s, and 113: 5863t all describe East German work on a process which also is based (at least in part) on the use of an auxiliary hydrocarbon. The first of the three of these describes what appears to be the application of conventional fractionation techniques to ultimately isolate a catecholrich distillate fraction. The second abstract further describes such fractionations, and also provides an explanation of a method very similar to that described in the above citation of Czechoslovakian work (104: 186131), except that the boiling range of the hydrocarbon fraction which is employed in this East German work is different (it is higher); it overlaps the boiling range of the hydrocarbon fraction used by the Czechoslovakians just a little. The third of these abstracts appears to offer further description of conventional fractionation techniques to isolate catechol (specifically, a catecholrich bottoms product), which is subjected to crystallization to improve purity.

Chemical Abstract Citation 104: 226658 describes the purification of catechol obtained from Phenosolvan extract by way of crystallization from aromatic hydrocarbons. This information on a German process was published in 1985.

SUMMARY OF THE INVENTION

The present invention employs an extractive distillation process using a high boiling polyol and most preferably glycerol for separating high purity catechol, 3-methylcatechol and/or 4-methylcatechol from a high boiling dihydric phenol fraction (a pitch-like material).

The first step consists of fractional distillation to first separate from the pitch an impure mixture of the catechol and 3-methylcatechol as an overhead. It should be noted that in a mixture such as this, 3-methylcatechol has a slightly higher boiling point than catechol, but not sufficiently higher boiling to permit separation of the two of these from each other by means of ordinary fractionation. The bottoms product from this step is then distilled to separate an impure 4-methylcatechol fraction from a residual material. The impure mixture of catechol and 3-methylcatechol is then extractively distilled with the glycerol to remove the impurities as an overhead. The catechol, 3-methylcatechol and glycerol bottoms product is then extractively distilled with additional glycerol to separate the 3-methylcatechol as an overhead, and the catechol and glycerol as a bottoms. The catechol is then distilled from the glycerol. The impure 4-methylcatechol, which was previously separated, is also extractively distilled with the glycerol to remove the impurities as an overhead. The 4-methylcatechol and glycerol mixture is then distilled to separate the purified 4-methylcatechol as an overhead from the glycerol.

DESCRIPTION OF THE PREFERRED EMBODIMENTS

Figure 1:
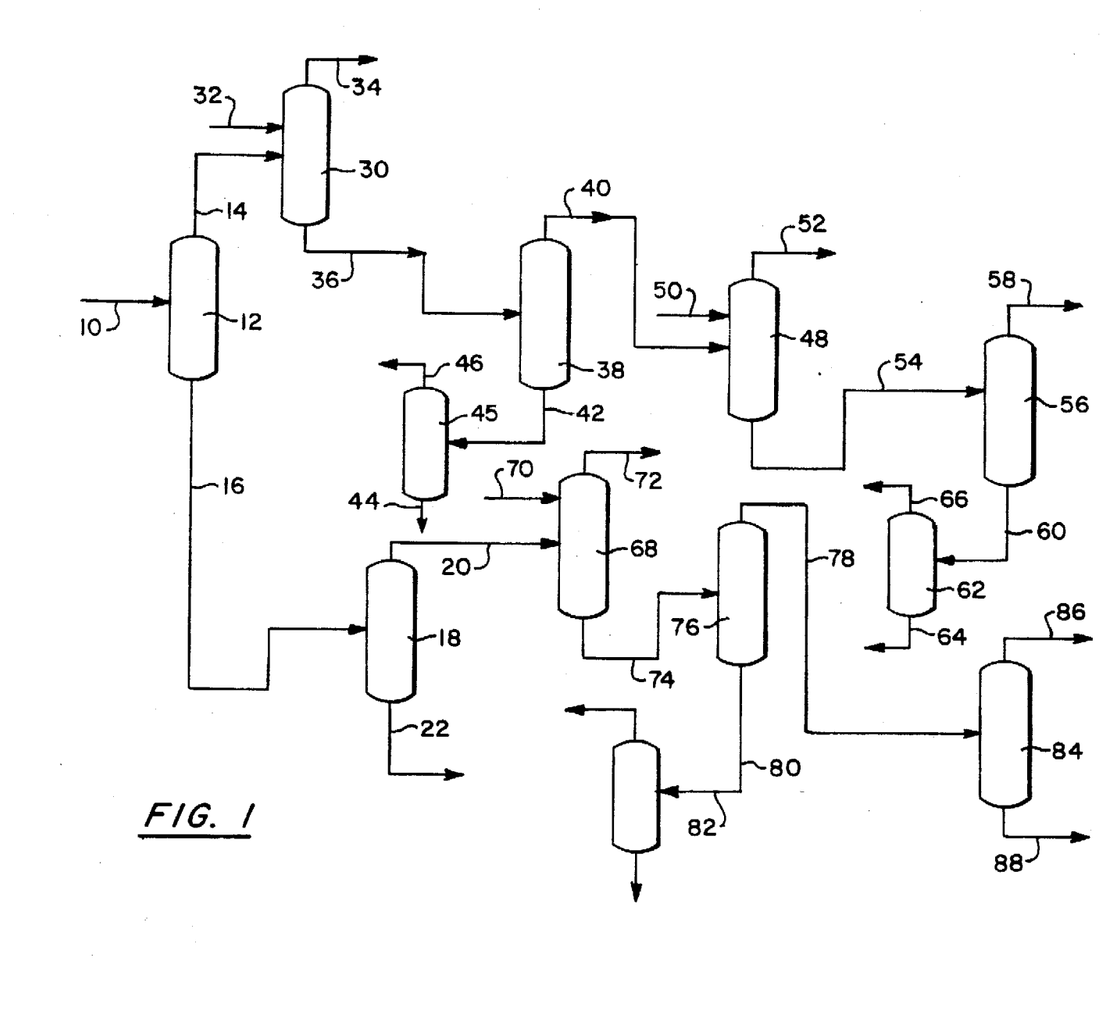
FIG. 1 is a process flow diagram illustrating the method of practicing the present invention.

Referring first to FIG. 1 of the drawings, a feed stream 10 consists of a pitch-like stream derived from a process for recovering monohydric phenols from Phenosolvan extract, or any similar feed stream of dihydric phenols. This feed stream is prepared for extractive distillation by a first distillation in column 12 which serves to separate, as an overhead product stream 14, the catechol and 3-methylcatechol together with essentially all of the impurities that are present having boiling points which are within and lower than the boiling range of the catechol and 3-methylcatechol including any remaining monohydric phenols such as these found in the high boiling end of cresylic acid. The bottoms stream 16 from the column 12 consists of the 4-methylcatechol and impurities having boiling points higher than the boiling range of the catechol and 3-methylcatechol including the highly sterically hindered $C_2$ catechols. By that, it is meant the $C_2$ catechols (e.g., dimethylcatechols) containing two methyl groups which are adjacent to (or near by) the two hydroxy (OH) groups, thus they "crowd" the hydroxy groups. Alternately, a $C_2$ catechol could be an ethylcatechol, which would necessarily be less hindered than the most hindered of the dimethylcatechols. For example, 3,6-dimethylcatechol would be highly hindered, whereas 4,5-dimethylcatechol would not be hindered. The more highly sterically hindered $C_2$ catechols have lower boiling points than those which are not hindered or are less hindered. It is important in this distillation step 12 to provide conditions which are capable of yielding a distillate which consists of catechol, 3-methylcatechol and impurities, with little or no $C_2$ catechol substances present, ideally less than 0.1% by weight. If the lightest boiling two $C_2$ catechols were present in the overhead 14, they would end up as contaminants in the finished product, since the downstream extractive distillation step would not be capable of removing them. The distillation step 12 must also provide a bottoms product 16 with as low a level as possible of the catechol and 3-methylcatechol, since the downstream extractive distillation that is used to purify the 4-methylcatechol will not effectively remove the catechol.

In practice, it is not possible to obtain a bottoms product 16 from the distillation column 12 which is as low in catechol and 3-methylcatechol content as would be desired. That is because the 4-methylcatechol and pitch fraction in the reboiler of column 12 undergoes thermally induced rearrangement or transalkylation reactions where aromatic ring-substituted methyl groups shift from one molecule to another. These inevitable transalkylations tend to supply traces of freshly created catechol and 3-methylcatechol in the reboiler and in the bottoms product stream 16.

The bottoms product stream 16 is fed to a second distillation column 18 where a raw, impure 4-methylcatechol fraction, containing the impurities having boiling points similar to and lower than the 4-methylcatechol including the above-mentioned light boiling, more sterically hindered $C_2$ catechols, is separated as an overhead product stream 20. The term "boiling points similar to" as used herein means boiling points so close to the mentioned material that separation by mere distillation is difficult or impossible. The bottoms product stream 22 from this column 18 consists of the higher boiling, less sterically hindered $C_2$ catechols and the remainder of the high boiling pitch residue substances. It is important in this second distillation to produce an overhead product stream 20 containing very low levels, ideally less than 0.1% by weight, of two higher boiling, less sterically hindered $C_2$ catechols, since it is not possible to separate them from the 4-methylcatechol in the downstream extractive distillation purification step. These two $C_2$ catechols have boiling points that are just a little higher than 4-methylcatechol itself, thus the separation of a 4-methylcatechol fraction from them is difficult.

Figure 2:
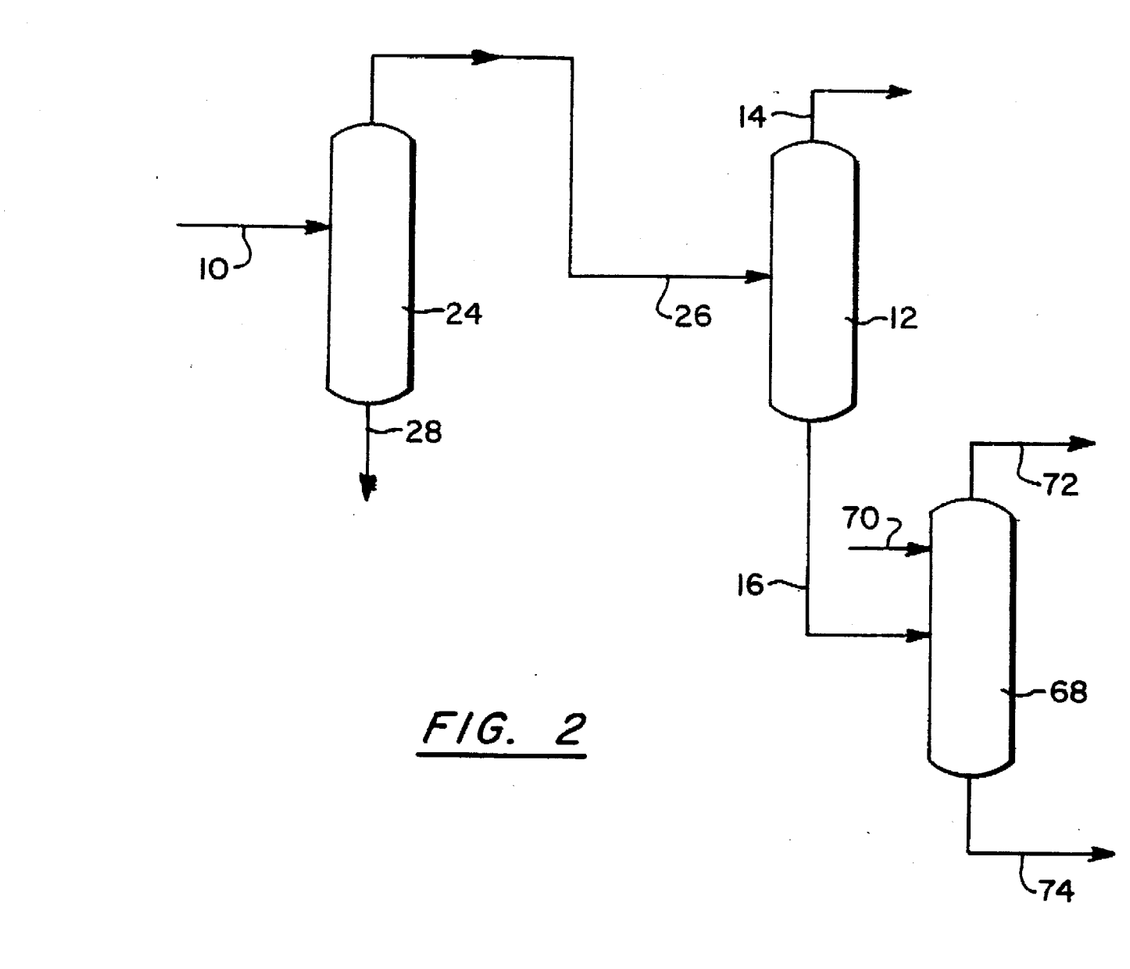
FIG. 2 is also a process flow diagram illustrating an alternate method of practicing a portion of the present invention and involving an additional purification step for the feed.
Figure 3:
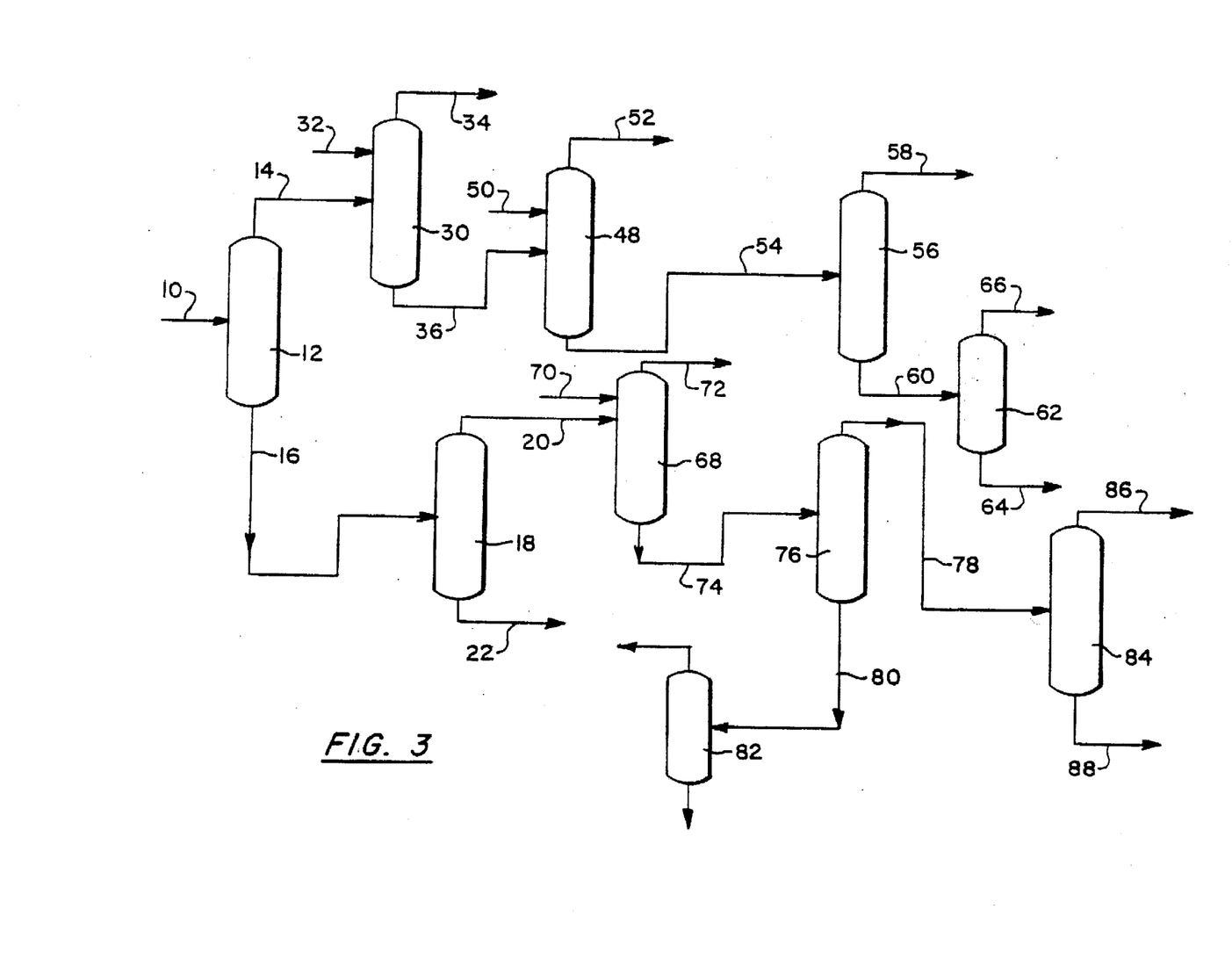
FIG. 3 is a process flow diagram illustrating an alternate method of practicing the present invention and involving an additional glycerol separation step.

FIG. 2 illustrates an alternate method which can be used to prepare the feed stream 10 for processing in the present invention. In this embodiment, the feedstream 10 is first fed to an initial distillation column 24 located prior to the distillation column 12 wherein the catechol, 3-methylcatechol and 4-methylcatechol are removed as an overhead product 26, and the higher boiling pitch and the two above-mentioned higher boiling $C_2$ catechols are separated as a bottoms 28. The advantage of this embodiment is that the three dihydric phenol products are immediately separated from the residual pitch. It is the pitch which supplies at least some of the raw material for the thermal rearrangements (transalkylations) that create catechol and 3-methylcatechol in the bottoms from the column 12. In this arrangement, the high boiling materials are first removed at 28 so that the raw 4-methylcatechol fraction which is obtained in the bottoms 16 from column 12 is even lower in catechol and 3-methylcatechol than would otherwise be provided. The alternate process as shown in FIG. 2 obviates the need for column 18 as shown in FIGS. 1 and 3, since this alternate process yields a depitched 4-methylcatechol stream 16 which is ready for feeding directly to column 68. Column 18 would be redundant, in the event of FIG. 2 processing, since it is a depitching column. It should be noted that the FIG. 2 processing in column 24 requires careful distillation control, so as to prevent the two earlier-mentioned $C_2$ catechols, which are slightly higher boiling than 4-methylcatechol, from being taken overhead.

Referring back to FIG. 1, the overhead 14 from the distillation column 12, containing catechol, 3-methylcatechol, and impurities, is fed to the extractive distillation column 30. Near the top of this column 30 is fed a solvent stream 32 of a high boiling polyol and most preferably glycerol. This solvent feed location near the top of the column is located below a length of (section of) column packing, which serves to wash any glycerol out of the ascending vapor phase, by means of the reflux to the column 30. The glycerol, which primarily descends the column as a liquid phase, has a greater tendency to hydrogen bond with the catechol and 3-methylcatechol than with any of the impurities, thereby inhibiting the volatility of the catechol and 3-methylcatechol. The tendency of the glycerol to hydrogen bond with the impurities is less, and their volatilities are less affected. This permits virtually all of the impurities to be removed as an overhead product 34 from this extractive distillation process. The bottoms product 36 from the column 30 is a mixture of the catechol, 3-methylcatechol and glycerol.

This bottoms stream 36 may be processed in either of two options, depicted in FIGS. 1 and 3. In FIG. 1, the stream 36 is fed first to a distillation column 38 where the purified mixture of catechol and 3-methylcatechol is separated as an overhead stream 40 from the bottoms stream 42, which contains the glycerol as well as process-created pitch-like materials. The bottoms stream 42 is then distilled at 45, a small minimally-refluxed still, to remove the pitch-like materials as a bottoms product 44, and recover the glycerol at 46 for recycle. The overhead 40 of purified catechol and 3-methylcatechol is then fed to the extractive distillation column 48.

The other option, depicted in FIG. 3, is for the stream 36 to be fed directly to the extractive distillation column 48 without the removal of glycerol. In the extractive distillation column 48 of FIG. 3 (which is actually receiving a different feed composition than the column 48 in FIG. 1 ), more glycerol is added at an appropriate solvent feed location 50 near the top of the column. The solvent extracts the catechol preferentially and the purified 3-methylcatechol is recovered as overhead stream 52. This extraction is possible due to the lower strength of the hydrogen bonding between glycerol and 3-methylcatechol than between glycerol and catechol. The bottoms product 54 from the column 48 is a mixture of catechol and glycerol. The catechol is more dilute in the glycerol solution stream 54 in the process of FIG. 3 than it would be in the arrangement of FIG. 1, since glycerol has been removed at 42 in the FIG. 1 arrangement. Although in the FIG. 1 embodiment the separation of catechol from 3-methylcatechol can be achieved at a lower solvent ratio in the extractive distillation column 48, the disadvantage is that it requires an additional distillation tower 38.

The bottoms 54 (in either FIG. 1 or FIG. 3) from the extractive distillation column 48, consisting of catechol and glycerol, is fed to the distillation column 56 where purified catechol is distilled off as the overhead 58. The glycerol bottoms stream 60 is fed to the small, minimally-refluxed still 62 to remove as bottoms product 64 the pitch-like material which tends to build up in the solvent. The overhead 66, which is glycerol free of pitch is then recycled to the front end of the process.

Returning now to the stream 20 (in either FIG. 1 or FIG. 3), consisting of the raw, impure 4-methylcatechol which contains the low boiling $C_2$ hindered catechols and will inevitably contain some small amounts of catechol and 3-methylcatechol, this stream is fed to the extractive distillation column 68. A glycerol solvent, fed at 70 near the top of this column 68, descends through the column primarily as a liquid phase. The glycerol preferentially hydrogen bonds with the 4-methylcatechol, permitting the impurities having boiling points similar to and lower than the 4-methylcatechol (the low boiling, highly hindered $C_2$ catechols, as well as other phenolic impurities, some neutral oil substances, and tar bases) to be removed as an overhead product 72. The bottoms product 74, consisting of the 4-methylcatechol and glycerol, is then fed to the recovery distillation column 76 where the 4-methylcatechol is obtained as the overhead product 78 and the glycerol is obtained as the bottoms product 80. Once again, the glycerol bottoms 80 is processed in the still 82 for depitching and recycle.

The overhead product 78 consists of the 4-methylcatechol, as well as a small amount of catechol, primarily present as a result of transalkylation reactions which have occurred. Also, the amount of high boiling, less hindered $C_2$ catechols which contaminate this 4-methylcatechol product will be dictated by the extent to which they were prevented from going overhead in the distillation column 18 (or alternately, in FIG. 2, distillation column 24). This overhead stream 78 is fed to the fractionation column 84 where the small amount of catechol which is present is removed as the light end 86, providing the 4-methylcatechol as bottoms stream 88. If needed, a flash distillation step can be performed on this bottoms product of 4-methylcatechol to improve its color.

Additionally, the process is appropriate for purification of catechol. A feedstock in this embodiment would be a reaction product of a synthetic route, and would consist of catechol and impurities which are a consequence of the synthetic route. If impurities having boiling points higher than that of catechol are present, then, this feedstock, which in this instance is the feed 10, is fed to column 12 of FIG. 1, to separate the catechol and impurities with boiling points similar to and lighter than catechol as an overhead product, from impurities boiling higher than catechol taken as a bottoms product. The overhead 14 is then extractively distilled in distillation column 30, with a polyol solvent 32 being fed to the column at a solvent feed location near the top of the column. The glycerol, which primarily descends the column as a liquid phase, preferentially hydrogen bonds with the catechol, thus inhibiting its volatility, relative to the impurities. This permits virtually all of the impurities to be removed as overhead stream 34. The bottoms 36, which is catechol and polyol solvent, is fed to distillation column 38. Here, the purified product catechol is separated as overhead 40, and the bottoms 42 is the polyol solvent, which is fed to the small, minimally-refluxed still 45, to separate the solvent 46 from process created pitch taken as a bottoms 44. Alternately, if no impurities are present in the synthetic catechol feed stream that are higher boiling than catechol, then the feed goes directly to the extractive distillation column 30, and the purification continues as described above for column 30 and subsequent steps. These two possible variations of the process of the present invention consist of only the relevant portion of FIG. 1, as cited above.

EXAMPLE

As one specific example of the present invention, reference will be made to FIG. 1 of the drawings. A Phenosolvan pitch steam 10 is fed at the rate of 11.3 kg per hour to a 15 cm diameter pilot plant continuous fractionation tower 12. The feed is to the 31st stage and the tower has 80 theoretical stages. The pressure profile across the tower packing is such that the overhead pressure is 4.0 kPa and the reboiler pressure is 10.7 kPa with a reboiler rate of 8,800 to 10,300 watts heat input. This rate of heat input includes that required for incidental heat losses from the system. After equilibrium is reached, collection of overhead product begins at a reflux ratio of 10:1. About 3.2 kg per hour of overhead product and 8.2 kg per hour of bottoms product are withdrawn. The overhead product 14 contains less than 0.05 wt. % of the highly hindered $C_2$ catechol specie which is the most difficult to remove, and even less of the other highly hindered $C_2$ catechol specie. The bottoms product 16 consists of the 4-methylcatechol and all of the high boiling pitch material. It also contains 0.20 wt. % catechol and 1.3 wt. % 3-methylcatechol.

The bottoms product 16 from the tower 12 is pumped to the 30th stage of a 15 cm diameter distillation tower 18, which is configured to have 85 stages. The feed rate is 13.6 kg per hour with an overhead pressure of 2.7 kPa, a reboiler pressure of 7.9 kPa, and a boilup rate in the range of 8,800 to 9,400 watts. After equilibration of this column 18, a reflux ratio of 15:1 is established. The overhead product 20 is collected at the rate of 2.7 kg per hour and the bottoms 22 is collected at the rate of 10.9 kg per hour. Conditions are such that the total of the two $C_2$ catechol species which are slightly higher boiling point than 4-methylcatechol is limited to 0.15 wt. % in the overhead product 20. This overhead product also contains the two lowest boiling $C_2$ catechol species, 2.0 wt. % catechol, and 2.3 wt. % 3-methylcatechol. The bottoms product 22 is of value as a boiler fuel or possibly as a feedstock for the recovery of $C_2$ catechol species.

The overhead 14 from the column 12 is fed at the rate of 10.0 kg per hour to the 21st stage of the 15 cm diameter extractive distillation tower 30 having a total of 35 stages. The glycerol stream 32 is fed to the 32nd stage, near the top of the column, at a solvent feed location which is 3 stages from the top of the column, at a rate of 20.0 kg per hour. The overhead pressure is 1.6 kPa and the reboiler pressure is 4.8 kPa while the boilup rate corresponds to a heat input in the range of 5,600 to 6,400 watts. The reflux ratio is set at 4:1 after equilibration. The overhead production 34 is 5.0 kg per hour and consists of high boiling cresylic acid, neutral oil, tar bases and only 0.1 wt % catechol and 0.5 wt. % 3-methylcatechol. The bottoms 36 is a mixture of glycerol, catechol and 3-methylcatechol, and is collected at the rate of 24.9 kg per hour.

The bottoms product 36 is fed to the 15th stage of the 15 cm diameter column 38 having a total of 30 stages. The overhead pressure is 1.6 kPa, the reboiler pressure is 4.1 kPa, and the boilup rate corresponds to a heat input in the range of 4,700 to 5,900 watts. After equilibration, a reflux ratio of 4:1 is employed. The overhead 40 of catechol and 3-methylcatechol contains 0.5 wt. % impurities, and is collected at the rate of 5.0 kg per hour. The solvent bottoms 42 contains 0.5 wt. % catechol and 0.1 wt. % 3-methylcatechol.

The overhead 40 is fed to the 32nd stage of the 15 cm diameter column 48 which has a total of 60 stages. The feed rate is 3.6 kg per hour, with a glycerol feed 50 of 29 kg per hour at the 54th stage. The overhead pressure is 1.7 kPa with a boilup rate corresponding to a heat input in the range of 6,400 to 7,000 watts. The reflux ratio is set at 8:1 and the overhead product 52 of purified 3-methylcatechol is collected at the rate of 1.6 kg per hour. This 3-methylcatechol has a catechol content of 1.1 wt. % and a total of 0.7 wt. % of other impurities. The bottoms product 54, consisting of the catechol and glycerol, is collected at the rate of 31.1 kg per hour. The bottoms stream 54 is fed to the 15th stage of the 30 stage tower 56, which is operated at an overhead pressure of 1.9 kPa, a reboiler pressure of 4.4 kPa, and at 6,400 to 7,000 watts. A reflux ratio of 14:1 is established and the overhead product 58 is collected at a rate of 2.0 kg per hour. The overhead 58 of the purified catechol contains only 0.2 wt. % 3-methylcatechol and 0.3 wt. % total other impurities. The bottoms 60 is glycerol with 0.1 wt. % catechol and is collected at a rate of 29 kg per hour.

Going back to the 4-methylcatechol fraction in stream 20, this stream is fed to a 15 cm diameter extractive distillation tower 68 at the 25th stage of a 61 stage configuration at the rate of 7.3 kg per hour. Glycerol is fed at 70 to the 48th stage at the rate of 24.9 kg per hour. The overhead pressure is 0.5 kPa, the reboiler pressure is 2.9 kPa, and the heat input is 4,100 to 4,700 watts. The reflux ratio is set at 7:1 and the overhead product 72 is collected at the rate of 5.0 kg per hour. This overhead impurities stream 72 contains some unknown phenolics, neutral oil, tar bases, 5.0 wt. % 4-methylcatechol, 0.3 wt. % catechol, 7.0 wt. % 3-methylcatechol, and the balance consists of other impurities. The bottoms stream 74 of glycerol and 4-methylcatechol also contains almost all of the catechol that was present in the stream 16, and is collected at the rate of 27.2 kg per hour. This is fed to the 15 cm diameter column 76 to the 15th stage of 30 stages. The overhead pressure is 0.5 kPa, the reboiler pressure is 4.8 kPa with a heat input in the range of 7,600 to 8,200 watts. A reflux ratio of 6.5:1 is set and the overhead product 78 is collected at the rate of 2.3 kg per hour. This overhead of purified 4-methylcatechol contains 4.0 wt. % catechol, negligible 3-methylcatechol and only 0.5 wt. % other impurities. The bottoms 80 of glycerol contains 0.5 wt. % 4-methylcatechol and is collected at the rate of 24.9 kg per hour. This material is fed to the depitching still 82 to prepare the solvent for recycle.

The overhead stream 78 of 4-methylcatechol, which contains some catechol, is fed at a rate of 45.5 kg per hour, to the fractionator 84 at the 15th stage of 30 stages. This number of states is sufficient, since the boiling point spread between catechol and 4-methylcatechol is significant. A reflux ratio of 22:1 is established, and overhead is collected at the rate of 2.0 kg per hour. The overhead pressure is 0.8 kPa, the reboiler pressure is 4.0 kPa, and the heat input is 6,400 to 7,300 watts. The 4-methylcatechol bottoms 88 contains only 0.03 wt. % catechol and 0.24 wt. % total other impurities, and is collected at the rate of 43.4 kg per hour. The catechol-rich overhead 86 contains 33 wt. % 4-methylcatechol, and is recycled to the front end of the overall process.

The above example is given merely to illustrate the present invention and how it might be operated in a specific situation using a pilot plant set-up. Various modifications can be made in the process and still come within the scope of the invention. For example, high boiling polyols other than the preferred glycerol might be used. Also, pressures other than those recited could be used, keeping in mind that higher pressures result in increased formation of process-created pitch and an increased propensity for transalkylation reactions to occur, while lower pressures result in the requirement for greater column diameters. Similarly, the other factors such as feed rates, reflux ratios, boilup rates, total number of stages employed and feed plate location could be modified.

We claim:

1. A method of processing a feedstock of a high boiling phenolic mixture containing catechol, 3-methylcatechol, 4-methylcatechol and impurities comprising the steps of:
   a) distilling said feedstock to produce a first overhead stream containing said catechol and said 3-methylcatechol and the impurities having boiling points within and lower than the boiling range of said catechol and 3-methylcatechol and being essentially free of the impurities having boiling points higher than said boiling range of said catechol and 3-methylcatechol and to further produce a first bottoms stream containing said 4-methylcatechol together with said impurities having boiling points higher than said boiling range of said catechol and 3-methylcatechol;
   b) distilling said first bottoms stream from step (a) to produce a second overhead stream containing said 4-methylcatechol and impurities having boiling points similar to and lower than said 4-methylcatechol but higher than said boiling range of said catechol and 3-methylcatechol, and being essentially free of impurities having boiling points higher than 4-methylcatechol;
   c) extractively distilling said second overhead stream from step (b) with a high boiling polyol to remove a third overhead stream containing said impurities having boiling points similar to and lower than said 4-methylcatechol but higher than said boiling range of said catechol and 3-methylcatechol and to provide a third bottoms stream containing said 4-methylcatechol and said high boiling polyol and subsequently recovering said 4-methylcatechol from said third bottoms stream and producing a stream containing said high boiling polyol;
   d) extractively distilling said first overhead stream from step (a) with a high boiling polyol to remove from said first overhead stream a fourth overhead stream containing said impurities with boiling points within and lower than said boiling range of said catechol and 3-methylcatechol and a fourth bottoms stream containing said catechol and said 3-methylcatechol from said first overhead stream and said high boiling polyol;
   e) extractively distilling said fourth bottoms stream from step (d) with a further quantity of high boiling polyol to remove a purified fifth overhead stream of said 3-methylcatechol from said fourth bottoms stream and a fifth bottoms stream containing said catechol from said fourth bottoms stream and said high boiling polyol;
   f) distilling said fifth bottoms stream from step (e) to recover a purified sixth overhead stream of said catechol from said fifth bottoms stream and a sixth bottoms stream containing said high boiling polyol.

2. A method as recited in claim 1 wherein said high boiling polyol is glycerol.

3. A method as recited in claim 1 and further including the additional step of distilling said fourth bottoms stream from step (d) prior to step (e) to remove from said fourth bottoms stream a stream containing said high boiling polyol.

4. A method as recited in claim 3 wherein said streams containing said high boiling polyol from steps (c) and (f) and from said additional step of distilling said fourth bottoms stream are purified by minimal reflux distillation and said purified high boiling polyol is recycled to said extractive distillation steps.

5. A method as recited in claim 3 wherein said high boiling polyol is glycerol.

6. A method as recited in claim 1 wherein said sixth bottoms stream containing said high boiling polyol from step (f) and said produced stream containing said high boiling polyol from step (c) are purified and said high boiling polyol is recycled to said extractive distillation steps.

7. A method as recited in claim 1 wherein said step of subsequently recovering said 4-methylcatechol from said third bottoms stream in step (c) comprises the steps of distilling said third bottoms stream to separate a seventh overhead stream of 4-methylcatechol and a seventh bottoms stream containing said high boiling polyol.

8. A method as recited in claim 7 wherein said seventh overhead stream of 4-methylcatechol contains a quantity of catechol and further comprises the step of separating said quantity of catechol from said 4-methylcatechol by distillation and recycling said quantity of catechol to said distillation step (a).

9. A method of processing a feedstock of a high boiling phenolic mixture containing catechol, 3-methylcatechol, 4-methylcatechol and impurities including highly hindered $C_2$ catechols and less hindered $C_2$ catechols comprising the steps of:
   a) distilling said feedstock to produce a first overhead stream containing said catechol and said 3-methylcatechol and the impurities having boiling points within and lower than the boiling range of said catechol and 3-methylcatechol and being essentially free of the impurities having boiling points higher than said boiling range of said catechol and 3-methylcatechol including said highly hindered $C_2$ catechols and said less hindered $C_2$ catechols and to further produce a first bottoms stream containing said 4-methylcatechol together with said impurities having boiling points higher than said boiling range of said catechol and 3-methylcatechol including such highly hindered $C_2$ catechols and said less hindered $C_2$ catechols;
   b) distilling said first bottoms stream from step (a) to remove a second bottoms stream containing impurities including said less hindered $C_2$ catechols and produce a second overhead stream containing said 4-methylcatechol and the impurities having boiling points similar to and lower than said 4-methylcatechol but higher than said boiling range of said catechol and 3-methylcatechol including said highly hindered $C_2$ catechols and being essentially free of impurities having boiling points higher than 4-methylcatechol including said less hindered $C_2$ catechols;

c) extractively distilling said second overhead stream from step (b) with a high boiling polyol to remove a third overhead stream containing said impurities having boiling points similar to and lower than said 4-methylcatechol including said highly hindered $C_2$ catechols and higher than said boiling range of said catechol and 3-methylcatechol and to provide a third bottoms stream containing said 4-methylcatechol and said high boiling polyol and subsequently recovering said 4-methylcatechol from said third bottoms stream and producing a stream containing said high boiling polyol;

d) extractively distilling said first overhead stream from step (a) with a high boiling polyol to remove a fourth overhead stream containing said impurities with boiling points within and lower than said boiling range of said catechol and 3-methylcatechol and a fourth bottoms stream containing said catechol and said 3-methylcatechol and said high boiling polyol;

e) extractively distilling said fourth bottoms stream from step (d) with a further quantity of high boiling polyol to remove a purified fifth overhead stream of said 3-methylcatechol and a fifth bottoms stream containing said catechol and said high boiling polyol;

f) distilling said fifth bottoms stream from step (e) to recover a purified sixth overhead stream of said catechol and a sixth bottoms stream containing said high boiling polyol.

10. A method as recited in claim 9 wherein said high boiling polyol is glycerol.

11. A method as recited in claim 9 and further including the additional step of distilling said fourth bottoms stream from step (d) prior to step (e) to remove from said fourth bottoms stream a stream containing said high boiling polyol.

12. A method as recited in claim 11 wherein said streams containing said high boiling polyol from steps (c) and (f) and from said additional step of distilling said fourth bottoms stream are purified by minimal reflux distillation and said purified high boiling polyol is recycled to said extractive distillation steps.

13. A method as recited in claim 11 wherein said high boiling polyol is glycerol.

14. A method as recited in claim 9 wherein said sixth bottoms stream containing said high boiling polyol from step (f) and said produced stream containing said high boiling polyol from step (c) are purified and said high boiling polyol is recycled to said extractive distillation steps.

15. A method as recited in claim 9 wherein said step of subsequently recovering said 4-methylcatechol from said third bottoms stream in step (c) comprises the steps of distilling said third bottoms stream to separate a seventh overhead stream of 4-methylcatechol and a seventh bottoms stream containing said high boiling polyol.

16. A method as recited in claim 15 wherein said seventh overhead stream of 4-methylcatechol contains a quantity of catechol and further comprises the step of separating said quantity of catechol from said 4-methylcatechol by distillation and recycling said quantity of catechol to said distillation step (a).

* * * * *